(12) United States Patent
Brazdil et al.

(10) Patent No.: US 12,065,417 B2
(45) Date of Patent: Aug. 20, 2024

(54) PROCESSES AND CATALYSTS FOR THE SELECTIVE HYDROGENATION OF COMPOUNDS HAVING CARBONYL CARBON ATOMS

(71) Applicant: Archer Daniels Midland Company, Decatur, IL (US)

(72) Inventors: James Brazdil, Glen Ellyn, IL (US); Chi-Cheng Ma, Champaign, IL (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 551 days.

(21) Appl. No.: 17/421,492

(22) PCT Filed: Jan. 9, 2020

(86) PCT No.: PCT/US2020/012912
§ 371 (c)(1),
(2) Date: Jul. 8, 2021

(87) PCT Pub. No.: WO2020/146618
PCT Pub. Date: Jul. 16, 2020

(65) Prior Publication Data
US 2022/0064136 A1    Mar. 3, 2022

Related U.S. Application Data

(60) Provisional application No. 62/791,216, filed on Jan. 11, 2019.

(51) Int. Cl.
*C07C 45/64* (2006.01)
*B01D 3/40* (2006.01)
*C07D 307/42* (2006.01)

(52) U.S. Cl.
CPC ............ *C07D 307/42* (2013.01); *B01D 3/40* (2013.01); *C07C 45/64* (2013.01)

(58) Field of Classification Search
CPC .............................. C07C 45/64; C07D 307/42
See application file for complete search history.

(56) References Cited

U.S. PATENT DOCUMENTS

| | | | |
|---|---|---|---|
| 2008/0207953 A1 | 8/2008 | Houssin et al. | |
| 2009/0143612 A1 | 6/2009 | Puckette et al. | |
| 2015/0152440 A1 | 6/2015 | Garcez Lopes et al. | |
| 2016/0002137 A1 | 1/2016 | Taarning et al. | |

FOREIGN PATENT DOCUMENTS

| | | |
|---|---|---|
| WO | WO/2009/144136 | 12/2009 |
| WO | WO/2018/112774 | 6/2018 |

*Primary Examiner* — Sikarl A Witherspoon
(74) *Attorney, Agent, or Firm* — Andrew F. Nilles

(57) ABSTRACT

Selective hydrogenation processes are disclosed that can upgrade impure feeds, such as those obtained from biomass and containing a number of small (e.g., 2-6 carbon atom) molecules having aldehyde and/or ketone carbon atoms. For example, whereas glycolaldehyde and its methylated derivative, hydroxyacetone (acetol) are both high value intermediates for certain downstream processing reactions, they are normally recovered in a condensate from pyrolysis of carbohydrates (e.g., aldose-containing sugars) together with glyoxal and its methylated derivative, pyruvaldehyde. The selective hydrogenation of these compounds bearing two carbonyl carbon atoms, without over-hydrogenation to ethylene glycol and propylene glycol, can increase the concentration of the desired intermediates. These beneficial effects of selective hydrogenation may be achieved through the use of a hydrogenation catalyst comprising noble metals such as Ru and Pt.

3 Claims, No Drawings

PROCESSES AND CATALYSTS FOR THE SELECTIVE HYDROGENATION OF COMPOUNDS HAVING CARBONYL CARBON ATOMS

CROSS-REFERENCE TO RELATED APPLICATIONS

This application is a national stage entry of International Application No. PCT/US20/12912, filed Jan. 9, 2020, which itself claims priority to U.S. Provisional Patent Application No. 62/791,216, filed Jan. 11, 2019, the contents of each are incorporated herein by reference.

TECHNICAL FIELD

The present invention from one perspective relates to methods and catalysts for the selective hydrogenation of compounds having at least two carbonyl carbon atoms, which may be aldehyde and/or ketone carbon atoms. From another perspective, the invention relates to methods and catalysts for increasing the amount of a selectively hydrogenated analog, such as glycolaldehyde from the selective hydrogenation of glyoxal, both of which may be initially present in an impure feed.

BACKGROUND ART

The long-term trend of increasing cost of many hydrocarbon feedstocks has created major incentives for seeking alternative sources to petroleum-based carbon for the production of many important and valuable chemical products. Biomass (material derived from living or recently living organisms) is viewed as a readily available, inexpensive supply of renewable, non-petroleum based carbon from which many such known, high value chemicals can be derived. The ability to convert biomass to fuels, chemicals, energy and other materials is expected to strengthen rural economies, decrease dependence on oil and gas resources, and reduce air and water pollution. The generation of energy and chemicals from renewable resources such as biomass also reduces the net liberation of carbon dioxide, a greenhouse gas, into the environment, from fossil-based sources of otherwise "sequestered" carbon.

Nonetheless, the development of sustainable technologies for the production, from renewable resources, of those chemicals that have conventionally only been made from petroleum-based carbon remains a significant challenge. For example, in recent years, the biodiesel industry has provided abundant crude glycerol as a byproduct of refining triglycerides in plant oils and animal fats. This glycerol can be purified to serve as a feedstock for producing propylene glycol (1,2-propanediol), a same carbon-numbered, known high value chemical from non-renewable resources. However, significant expense resides in the steps needed to adequately purify glycerol for this purpose, and the biodiesel industry is heavily dependent on tax credits and other forms of governmental subsidies for its profitability.

The thermal decomposition of biomass is increasingly being investigated as a potential route for yielding smaller, so-called "platform" molecules that can serve as the building blocks for commercially desirable products. An important example of such a molecule is glycolaldehyde ($C_2H_4O_2$), having significant utility as a reactive intermediate, insofar as it is the smallest molecule having both aldehyde and hydroxyl carbon atoms. This molecule offers a potential synthesis pathway, through reductive amination, for the production of biobased monoethanolamine (MEA) and diethanolamine (DEA), having considerable industrial applications. Glycolaldehyde may be obtained from the conversion of aldose monomeric sugars (e.g., glucose), through the initial formation of an aqueous solution, followed by thermal decomposition ("hydrous thermolysis") and then condensation of the generated vapors. Such a process is described, for example, in WO 02/40436. In these and other thermal decomposition processes, also referred to in the art as pyrolysis and cracking processes, a rather diverse mixture of compounds is obtained, with each individual compound having varying reactivity and value as an intermediate. The separation of desired compounds can be complicated by the number of other compounds present in the condensate, as well as their similarities in terms of boiling point (relative volatility), which decreases the efficiency with which distillation can be used.

The overall economic attractiveness of a given synthesis route based on renewable carbon precursors, such as in the conversion of glycolaldehyde to MEA and DEA as described, for example, in U.S. Pat. Nos. 6,534,441, 8,772,548 and 8,742,174, is highly dependent on its total utility and energy requirements. These requirements, in turn, are greatly impacted by the upstream economics associated with refining an impure feed to obtain a product of the precursor, such as glycolaldehyde, having suitable purity. Progress in the ongoing efforts towards replacing fossil-derived chemicals with their renewable carbon counterparts will therefore rely heavily on improvements in upstream processing efficiency, particularly improvements that are realized from increased reaction selectivity, intermediate and final product quality, and/or component separability, all of which have the potential to reduce manufacturing costs to the point of commercial viability.

SUMMARY OF THE INVENTION

Aspects of the invention relate to the discovery of selective hydrogenation processes that can significantly benefit, or upgrade, impure feeds obtained from biomass, such as those feeds containing a number of small (e.g., 2-6 carbon atom) molecules having aldehyde and/or ketone carbon atoms. For example, whereas glycolaldehyde and its methylated derivative, hydroxyacetone (acetol) are both high value intermediates for certain downstream processing reactions, they are normally recovered in a condensate from pyrolysis of carbohydrates (e.g., aldose-containing sugars) together with glyoxal and its methylated derivative, pyruvaldehyde. These latter, more reactive species can interfere with the desired subsequent reactions, such as reductive amination of glycolaldehyde to MEA and/or DEA. For example, under conditions otherwise suitable for this reaction, these more reactive species can cause the production of unwanted imidazole derivatives. More specifically, in the presence of water or methanol as a solvent, ammonia in a high pressure hydrogen environment may combine with glycolaldehyde and either of the more reactive species, glyoxal or pyruvaldehyde, according to undesired cyclization reactions, such as:

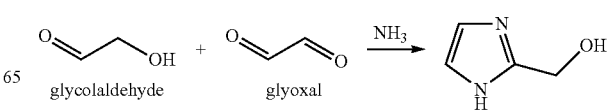

-continued

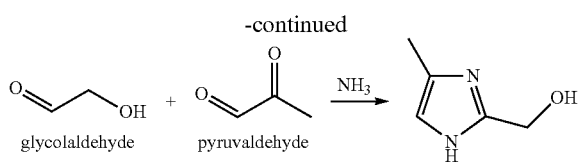

These and other reactions can not only significantly decrease the utilization of glycolaldehyde and other desired intermediates, such as hydroxyacetone (acetol), but also simultaneously produce byproducts that require downstream separation and consequently added production costs.

Advantageously, however, it has been found that the more reactive species generated in pyrolysis and other biomass conversion processes can be selectively hydrogenated to analogs, and particularly hydroxyl carbon atom analogs, which do not pose the above-noted potential to interfere with synthesis pathways involving desired intermediates (e.g., glycolaldehyde or hydroxyacetone). In fact, according to some embodiments, the selectively hydrogenated analogs may actually correspond to these desired intermediates themselves, such that selective hydrogenation can increase their amounts in a given product, thereby improving their effective availability for downstream processing while diminishing the potential for the detrimental formation of byproducts from more the reactive species, or starting compounds, as described herein.

Particular aspects of the invention are associated with the discovery of process conditions and catalysts for performing selective hydrogenation of one or more starting compounds to form a product having an increased amount of one or more desired intermediate(s) (e.g., glycolaldehyde and/or hydroxyacetone), corresponding to selectively hydrogenated analogs (e.g., hydroxyl carbon atom analogs). Advantageously, the selective hydrogenation is therefore generally accompanied by a decreased amount of one or more starting compound(s) (e.g., glyoxal and/or pyruvaldehyde) having the potential to reduce the effective availability of such desired intermediate(s), for example through the formation of unwanted byproducts as described above. The starting compounds that are selectively converted (selectively hydrogenated) are generally those exhibiting high reactivity by virtue of possessing at least two (and often only two) carbonyl carbon atoms, which may be aldehyde carbon atoms, ketone carbon atoms, or a combination of these.

For example, the starting compound glyoxal has two aldehyde carbon atoms, whereas the starting compound pyruvaldehyde has an aldehyde carbon atom and a ketone carbon atom. The selective hydrogenation of glyoxal, by converting one of its two aldehyde carbon atoms to a hydroxyl carbon atom, produces glycolaldehyde as a selectively hydrogenated analog. The selective hydrogenation of pyruvaldehyde, by converting its (more reactive) aldehyde carbon atom to a hydroxyl carbon atom, produces hydroxyacetone as a major selectively hydrogenated analog. Another, minor selectively hydrogenated analog, namely 2-hydroxy propanal, may also be produced, in this case by converting its (less reactive) ketone carbon atom to a hydroxyl carbon atom. Representative impure feeds may comprise other compounds, such as compounds having only a single carbonyl carbon atom (e.g., single aldehyde carbon atom or single ketone carbon atom) that may be converted in selective hydrogenation processes described herein to a hydroxyl carbon atom. An example of such a compound is 5-hydroxymethylfurfural, which may be converted to 2,5-dihydroxymethylfuran.

Advantageously, the use of selective hydrogenation conditions and catalysts described herein can provide a suitable reaction environment, whereby the most reactive compounds in an impure feed, and therefore those most susceptible to hydrogenation, are converted to more desirable (higher value) intermediates as described above. These intermediates themselves, however, whether produced by this selective hydrogenation, or initially present in the impure feed, are hydrogenated to a minimal or even negligible extent. The overall effect of subjecting the impure feed to the hydrogenation reaction environment, therefore, is generally to form a product having a net increase, or additional amount, of one or more of these higher value selectively hydrogenated analogs. That is, the further conversion (hydrogenation) of these more desirable intermediates to more completely, or completely, hydrogenated analogs in which additional, or all, carbonyl carbon atoms are converted to hydroxyl carbon atoms is limited or substantially absent.

For example, glyoxal may be substantially converted to glycolaldehyde but with minimal or negligible, further conversion (hydrogenation) of glycolaldehyde (whether produced from the glyoxal or already existing in the impure feed) to ethylene glycol. Likewise, pyruvaldehyde may be substantially converted to hydroxyacetone and/or 2-hydroxy propanal, but with minimal or negligible, further conversion (hydrogenation) of either or both of these selectively hydrogenated analogs to propylene glycol.

Using the teachings herein, the skilled person can determine the optimal hydrogenation environment (i.e., can tailor hydrogenation conditions) to achieve the selective conversion of one or more compounds in a given, impure feed, having a relatively high susceptibility to hydrogenation, to one or more higher value intermediates having a relatively low susceptibility to hydrogenation. This allows a product to be formed, having an increased amount of such intermediates, preferably without further conversion of such intermediates to a significant extent. In this manner, selective hydrogenation as described herein may, in some embodiments, comprise "selective stabilization," according to which an impure feed is beneficially stabilized by selective hydrogenation of the most reactive compounds, thereby (i) limiting, in downstream processing, unwanted side reactions of these compounds while also (ii) producing, from these compounds, an additional amount of higher value intermediates used in this downstream processing. Overall economics associated with providing the intermediate(s) in the synthesis of chemicals from renewable carbon sources may thereby be significantly improved.

Additional benefits of selective hydrogenation processes, and their associated conditions and catalysts, reside in the conversion of starting compounds to their selectively hydrogenated analogs, as described above, having significantly different relative volatility. Differences in the boiling points of the higher value intermediates can improve downstream vapor/liquid separation efficiency, such as in separation by distillation. In view of this, further aspects of the invention relate to synthesis methods including downstream, and optionally upstream, processing steps, which methods benefit from selective hydrogenation to increase the effective availability of one or more higher value intermediates, as described above. These methods, for example, can include upstream pyrolysis of a carbohydrate (e.g., aldose-containing sugar) and cooling to condense a liquid mixture, which is subjected to selective hydrogenation. The methods can also include downstream distillation of the resulting product of selective hydrogenation, to recover a fraction enriched in the higher value intermediate(s) (e.g., glycolaldehyde and/or hydroxyacetone).

Overall, selective hydrogenation using heterogeneous catalysts and conditions as described herein can serve an important or even essential role in establishing the economic viability required for the commercial scale production of renewable carbon-based chemicals. In addition to its environmental friendliness, selective hydrogenation is beneficial in terms of its low generation of hazardous waste compared to alternative pathways such as reduction processes that rely on stoichiometric quantities of reducing agents such as alkali metal borohydrides.

These and other aspects, embodiments, and associated advantages will become apparent from the following Detailed Description.

DETAILED DESCRIPTION OF EMBODIMENTS

Particular embodiments of the invention are directed to methods for the selective hydrogenation of at least a first starting compound present in an impure feed, in which the first starting compound has at least two carbonyl carbon atoms. The term "impure feed" is meant to convey that the starting compound is generally not present in its pure form and may often be in a mixture with other compounds obtained from a given application, such as the pyrolysis of carbohydrates. This term is not meant to provide any limitation on purity, and indeed selective hydrogenation methods described herein are equally applicable to feeds of high purity, such as a feed comprising 99 wt-% or more of a given starting compound as described herein, or a feed comprising one or more starting compounds and an aqueous or organic solvent (e.g., methanol) in a combined amount of 99 wt-% or more.

Representative methods comprise contacting the impure feed with a hydrogenation catalyst under hydrogenation conditions, to selectively hydrogenate the first starting compound to at least a major first selectively hydrogenated analog. This analog is produced namely by converting one of the at least two carbonyl carbon atoms to a hydroxyl carbon atom, while preserving another of the at least two carbonyl carbon atoms. Preferably, therefore, the remainder of the molecule of the first starting compound, aside from converting a single carbonyl carbon atom to a hydroxyl carbon atom, is unchanged (preserved). Selective hydrogenation thereby forms a product having an increased amount (e.g., increased concentration or percentage by weight) of the at least major first selectively hydrogenated analog. This "increased amount," as described above, refers to an increased overall amount, or increased net amount, considering any losses of this analog due to its further conversion (hydrogenation) to a more completely, or completely, hydrogenated analog in which additional, or all, carbonyl carbon atoms are converted to hydroxyl carbon atoms. Such further conversion may therefore pertain to this analog, as produced from the first starting compound or otherwise as already existing in the impure feed, since molecules of a given compound in this feed are generally not distinguishable on the basis of their origin. In an analogous manner, the product may have a decreased amount (e.g., decreased concentration or percentage by weight) of the first starting compound.

A "carbonyl carbon atom" of a given compound, as is recognized in the art, refers to a carbon atom that is double bonded to an oxygen atom. A carbonyl carbon atom may therefore refer to a carbon atom that forms an aldehyde group, in which the carbon atom is further bonded to both another carbon atom and a hydrogen atom, i.e., an "aldehyde carbon atom," as referenced herein. A carbonyl carbon atom may also refer to a carbon atom that forms a ketone group, in which the carbon atom is further bonded to two other carbon atoms, i.e., a "ketone carbon atom," as referenced herein.

Starting Compounds and their Selectively Hydrogenated Analogs

A selectively hydrogenated analog of a starting compound refers to a compound that is formed upon hydrogenation of one or more, but not all, of the carbonyl carbon atoms of the starting compound. This hydrogenation results in the conversion of the one or more carbonyl carbon atoms to one or more, corresponding hydroxyl carbon atoms. Often, aside from this conversion of the one or more carbonyl carbon atoms, the remainder of the selectively hydrogenated analog is preserved from the molecular structure of the starting compound. A "hydroxyl carbon atom," as is recognized in the art, refers to a carbon atom that is bonded to a hydroxyl (—OH) group. Often, a starting compound will have two carbonyl carbon atoms (e.g., two aldehyde carbon atoms, an aldehyde carbon atom and a ketone carbon atom, or two ketone carbon atoms), the selective hydrogenation of which results in the conversion of one of the two carbonyl carbon atoms to a corresponding hydroxyl carbon atom.

To emphasize that different starting compounds, having the characteristics of a "starting compound" as described above, may be present in a given impure feed, these may be designated as a "first starting compound," a "second starting compound," etc. Therefore, the "first starting compound" has at least two carbonyl carbon atoms as described above, such as at least two aldehyde carbon atoms, at least one aldehyde carbon atom and at least one ketone carbon atom, or at least two ketone carbon atoms. Any of such designated "starting compound," however, may be selectively hydrogenated in the same manner to form a selectively hydrogenated analog (e.g., an aldehyde carbon atom may be converted to a hydroxyl carbon atom and a ketone carbon atom may be preserved), and with the same performance criteria (e.g., in terms of the obtained yield), as described herein.

To emphasize that different selectively hydrogenated analogs may be produced from a given starting compound, such as different selectively hydrogenated analogs that may be produced from a "first starting compound" or different selectively hydrogenated analogs that may be produced from a "second starting compound." these different selectively hydrogenated analogs may be designated as a "major first selectively hydrogenated analog" or a "minor first selectively hydrogenated analog" (in the case of being produced from a first starting compound) or may be designated as a "major second selectively hydrogenated analog" or a "minor second selectively hydrogenated analog" (in the case of being produced from a second starting compound). The designations of "major" and "minor" may in some embodiments, but do not necessarily, refer to selectively hydrogenated analogs being produced in relatively higher and lower amounts (e.g., with higher and lower selectivities and corresponding yields), respectively.

For example, a "major first selectively hydrogenated analog" may be produced from the conversion of a more reactive aldehyde carbonyl carbon atom of a first starting compound to a corresponding hydroxyl carbon atom, while preserving a less reactive ketone carbon atom, whereas a "minor first selectively hydrogenated analog" may be produced from the conversion of a less reactive ketone carbon atom of the same, first starting compound to a corresponding hydroxyl carbon atom, while preserving a more reactive aldehyde carbon atom. In a manner analogous to such embodiment in which the impure feed comprises a first starting compound having both aldehyde and ketone carbon atoms, in which the conversion of the former produces a major first selectively hydrogenated analog and conversion of the latter produces a minor first selectively hydrogenated analog, the impure feed may further comprise other starting compounds having the having the characteristics of a "starting compound" as described above. For example, the impure feed may further comprise a second starting compound, different from the first starting compound but nonetheless having at least two carbonyl carbon atoms. The contacting of the impure feed with the hydrogenation catalyst under hydrogenation conditions as described herein may, in this case, selectively hydrogenate the second starting compound to at least a major second selectively hydrogenated analog, by converting one of the at least two carbonyl carbon atoms of the second starting compound to a hydroxyl carbon atom while preserving another of the at least two carbonyl carbon atoms of the second starting compound.

According to particular embodiments, two of the least two carbonyl carbon atoms of the first starting compound are aldehyde carbon atoms, with a specific example of such first starting compound being glyoxal. In the case such first starting compound, the first selectively hydrogenated analog (or major first selectively hydrogenated analog) may be produced (e.g., product may be formed, having an increased amount of the first selectively hydrogenated analog) by converting one of these aldehyde carbon atoms to a hydroxyl carbon atom, while preserving the other aldehyde carbon atom. According to a specific example, the selective hydrogenation of glyoxal produces glycolaldehyde as the selectively hydrogenated analog, based on the reaction:

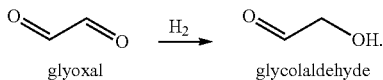

glyoxal          glycolaldehyde

According to other particular embodiments, one of the at least two carbonyl carbon atoms of the first starting compound is an aldehyde carbon atom and the other of the at least two carbonyl carbon atoms is a ketone carbon atom, with a specific example of such first starting compound being pyruvaldehyde. In the case of such first starting compound, the major first selectively hydrogenated analog may be produced (e.g., product may be formed, having an increased amount of the major first selectively hydrogenated analog) by converting the aldehyde carbon atom to a hydroxyl carbon atom, while preserving the ketone carbon atom. According to a specific example, the selective hydrogenation of pyruvaldehyde produces hydroxyacetone as the major first selectively hydrogenated analog, based on the reaction:

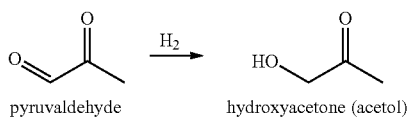

pyruvaldehyde          hydroxyacetone (acetol)

In the case of such first starting compounds (e.g., pyruvaldehyde) having both aldehyde and ketone carbon atoms, it is also possible to produce (e.g., form a product, having an increased amount of) a minor first selectively hydrogenated analog, by converting the ketone carbon atom to a hydroxyl carbon atom, while preserving the aldehyde carbon atom. According to a specific example, the selective hydrogenation of pyruvaldehyde produces 2-hydroxy propanal as the minor first selectively hydrogenated analog, based on the reaction:

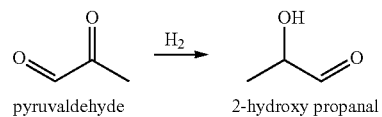

pyruvaldehyde          2-hydroxy propanal

Particular examples of starting compounds (e.g., first and/or second starting compounds) present in an impure feed are those obtained from the thermal decomposition of carbohydrates, including sugars such as those within the categories of aldose-containing sugars (e.g., glucose) and/or oligosaccharides (e.g., disaccharides such as sucrose). Such thermal decomposition yields smaller molecules. In representative embodiments, the first starting compound has, or optionally both the first starting compound and a second starting compound have, from 2 to 5 carbon atoms. In further representative embodiments, the first starting compound has, or optionally both the first starting compound and a second starting compound have, two carbonyl carbon atoms, for example only two carbonyl carbon atoms (e.g., only two aldehyde carbon atoms, only one aldehyde carbon atom and one ketone carbon atom, or only two ketone carbon atoms). According to a particular embodiment, the impure feed may comprise both glyoxal and pyruvaldehyde as first and second starting compounds, each having the characteristics of a "starting compound" as described herein.

Impure Feed/Product/Conversion of Starting Compounds and Other Compounds

A starting compound (e.g., a first starting compound), or mixture of starting compounds (e.g., a first starting compound and a second starting compound), may be present in the impure feed in an amount, or combined amount, that is representative of liquid mixtures condensed from vapor phase products of a carbohydrate pyrolysis, for example, but without limitation, a carbohydrate pyrolysis as described in WO 02/40436 referenced above. However, whether or not the impure feed is obtained from pyrolysis, the amount, or combined amount, may be generally from about 1 wt-% to about 75 wt-%, typically from about 2 wt-% to about 50 wt-%, and often from about 5 wt-% to about 30 wt-%. As described above, contacting of the impure feed with the hydrogenation catalyst under hydrogenation conditions converts (or, more specifically, selectively hydrogenates) the at least first starting compound to form a product having an increased amount of a selectively hydrogenated analog. According to more particular embodiments, this increased amount is relative to an initial amount of the selectively hydrogenated analog that is present in the impure feed. For example, selectively hydrogenated analog(s) of a given starting compound (e.g., a major first selectively hydrogenated analog and/or a minor first selectively hydrogenated analog of a first starting compound) may be present in the impure feed in an amount, or combined amount, within the ranges as described above with respect to the starting compound, or mixture of starting compounds. The increased amount of a selectively hydrogenated analog (e.g., in the case of a first starting compound, the increased amount of a major first selectively hydrogenated analog, the increased amount of a minor first selectively hydrogenated analog, or the increased amount of these selectively hydrogenated analogs in combination) may represent a yield, obtained from conversion (or, more specifically, selective hydrogenation) of the starting compound, of at least about 60% (e.g., from about 60% to 100%), at least about 75% (e.g., from about 75% to about 99%), or at least about 85% (e.g., from about 85% to about 99%), of a theoretical yield.

As is understood in the art, the yield of a given compound or compounds refers to the product of conversion and selectivity, with selectivity referring to the fraction (or percentage) of the converted product that manifests as that compound or those compounds. In determining a given yield, those skilled in the art will appreciate, using the teachings herein, that a given starting compound, selectively hydrogenated analog, or completely hydrogenated analog, may undertake various forms, such as dimer, oligomer, and hydrated forms, depending on the particular composition in which the compound and/or analog is contained (e.g., in the presence of an aqueous solvent or organic solvent). For example, glycolaldehyde may undertake any of dimer, oligomer, and hydrated forms. Glycolaldehyde dimer is a particularly prevalent form, and this form is also known as the ringed structure, 2,5-dihydroxy-1,4-dioxane. Therefore, for purposes of determining yields as described herein, one mole of a dimer of a compound or analog is considered equivalent to two moles of such compound or analog, one mole of a trimer of a compound or analog is considered equivalent to three moles of such compound or analog, etc.

For illustrative purposes, an exemplary impure feed may comprise 100 moles of pyruvaldehyde as a first starting compound. In this case, an increased amount, in the product, of (i) 80 moles of hydroxyacetone (acetol) as a major first selectively hydrogenated analog, or (ii) 80 moles of 2-hydroxy propanal as a minor first selectively hydrogenated analog, or (iii) 80 moles of these selectively hydrogenated analogs in combination, would represent 80% of the theoretical yield of, respectively, hydroxyacetone (acetol), 2-hydroxy propanal, or combination, obtained from conversion of pyruvaldehyde. These yields, associated with the increased amount, are in this case obtained regardless of whether the impure feed further comprises initial amounts of any of the first selectively hydrogenated analog (in this case hydroxyacetone (acetol)) and/or minor first selectively hydrogenated analog (in this case 2-hydroxy propanal).

Advantageously, as described above, the increased amount associated with "selective" hydrogenation relates to the discovery of hydrogenation conditions that do not cause a significant extent of more complete hydrogenation of the desired, selectively hydrogenated analogs, whether initially present in the impure feed or produced from their respective starting compounds. In representative embodiments, an amount, in the product, of more completely, or completely, hydrogenated analogs (in which additional, or all, carbonyl carbon atoms are converted to hydroxyl carbon atoms) represents a yield of such analogs of less than about 5% (e.g., from about 0.001% to about 5%), less than about 2% (e.g., from about 0.001% to about 2%), or less than about 1% (e.g., from about 0.01% to about 1%), of a theoretical yield. Such amounts of more completely, or completely, hydrogenated analogs may be obtained in combination with the increased amount of a selectively hydrogenated analog (or selectively hydrogenated analogs in combination) that represents a yield within any of the ranges described above. For illustrative purposes, the exemplary impure feed described above, comprising 100 moles of pyruvaldehyde as a first starting compound, may further comprise 20 moles of hydroxyacetone (acetol) as a major first selectively hydrogenated analog and 10 moles of 2-hydroxy propanal as a minor first selectively hydrogenated analog. Complete hydrogenation of this first starting compound and first selectively hydrogenated analogs could theoretically yield 130 moles of the completely hydrogenated analog, propylene glycol. Therefore, an amount of 1 mole of propylene glycol in the product would represent a yield of 0.77% (1/130) of the theoretical yield, assuming that the impure feed comprises no initial amount of this completely hydrogenated analog. In the case of the impure feed comprising an initial amount of a completely hydrogenated analog, then an increased amount (relative to the initial amount) would represent yields within the ranges given above (e.g., less than about 2% of a theoretical yield).

In view of the above description, according to some embodiments, the impure feed may comprise one or more selectively hydrogenated analogs (e.g., the major first selectively hydrogenated analog and/or minor first selectively hydrogenated analog), for example in an amount, or combined amount, within the ranges given above (e.g., from about 1 wt-% to about 75 wt-%), with respect to the amount, or combined amount, of a starting compound, or mixture of starting compounds. Otherwise, one or more selectively hydrogenated analogs may be substantially absent from the impure feed, for example, the one or more selectively hydrogenated analogs (e.g., the major first selectively hydrogenated analog and/or minor first selectively hydrogenated analog) may be present in the impure feed in an amount, or combined amount, of less than about 1 wt-%, or less than about 0.5 wt-%. Also, the impure feed may comprise one or more completely hydrogenated analogs (e.g., ethylene glycol in the case of glycolaldehyde as a starting compound and propylene glycol in the case of pyruvaldehyde as a starting compound), for example in an amount, or combined amount, within the ranges given above (e.g., from about 1 wt-% to about 75 wt-%), with respect to the amount, or combined amount, of a starting compound, or mixture of starting compounds. Otherwise, one or more completely hydrogenated analogs may be substantially absent from the impure feed, for example, the one or more completely hydrogenated analogs may be present in the impure feed in an amount, or combined amount, of less than about 1 wt-%, or less than about 0.5 wt-%.

In addition to the starting compound(s), the impure feed may comprise one or more compounds having (unlike the starting compound(s)) only a single carbonyl carbon atom that is either an aldehyde carbon atom or a ketone carbon atom. Under the hydrogenation conditions described herein (conditions of contacting the impure feed with the hydrogenation catalyst) such compound(s) may be hydrogenated to corresponding hydrogenated analog(s), by converting the single carbonyl carbon atom to a hydroxyl carbon atom. According to specific examples of compounds having only a single carbonyl carbon atom, the hydrogenation of furfural or 5-hydroxymethylfurfural may produce, respectively, 5-hydroxymethylfuran or 2,5-dihydroxymethylfuran as the corresponding hydrogenated analogs, based on the reactions:

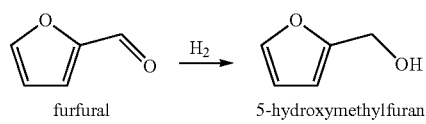

furfural      5-hydroxymethylfuran

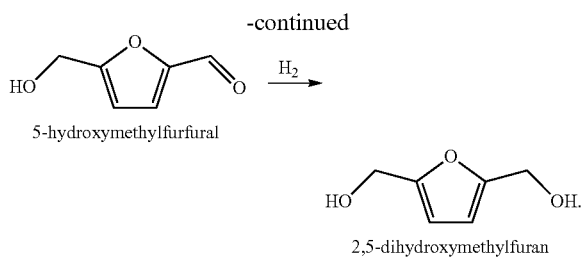

According to some embodiments, under the hydrogenation conditions suitable for substantially converting a starting compound (e.g., first starting compound) to one or more selectively hydrogenated analogs (e.g., major first selectively hydrogenated analog and/or minor first selectively hydrogenated analog) the one or more compounds having only a single carbonyl carbon atom may be partially converted to their corresponding hydrogenated analog(s). For example, the one or more corresponding hydrogenated analogs may be produced in an amount (to form a product having an increased amount) that represents a yield, obtained from conversion (hydrogenation) of such compound(s), of generally from about 10% to about 90%, typically from about 15% to about 75%, and often from about 20% to about 60%, of a theoretical yield. In such embodiments, the increased amount of one or more selectively hydrogenated analogs may represent a yield, obtained from conversion of one or more starting compounds, as described above (e.g., at least about 60% of a theoretical yield). The amount, or combined amount, in the impure feed, of one or more compounds having only a single carbonyl carbon atom, may be within the ranges given above (e.g., from about 1 wt-% to about 75 wt-%), with respect to the amount, or combined amount, of a starting compound, or mixture of starting compounds. Otherwise, the one or more compounds having only a single carbonyl carbon atom may be substantially absent from the impure feed, for example, such compounds may be present in the impure feed in an amount, or combined amount, of less than about 1 wt-%, or less than about 0.5 wt-%.

Regardless of whether one or more compounds having only a single carbonyl carbon atom are present in the impure feed or substantially absent, the impure feed may comprise one or more corresponding hydrogenated analogs of such compound(s) (e.g., 5-hydroxymethylfuran or 2,5-dihydroxymethylfuran as the corresponding hydrogenated analogs, respectively, of furfural or 5-hydroxymethylfurfural) in an amount, or combined amount, within the ranges given above (e.g., from about 1 wt-% to about 75 wt-%), with respect to the amount, or combined amount, of a starting compound, or mixture of starting compounds. Otherwise, one or more corresponding hydrogenated analogs may be substantially absent from the impure feed, for example, the one or more corresponding hydrogenated analogs may be present in the impure feed in an amount, or combined amount, of less than about 1 wt-%, or less than about 0.5 wt-%.

In yet further embodiments, value may be derived from conversion (hydrogenation) of such one or more compounds having only a single carbonyl carbon atom (e.g., furfural and/or 5-hydroxymethylfurfural), even in the absence or substantial absence of conversion (selective hydrogenation) of one or more starting compounds as described herein.

According to such embodiments, starting compounds as defined herein may be substantially absent in the impure feed, for example, starting compounds (e.g., compounds having at least two carbonyl carbon atoms, such as those having only two carbonyl carbon atoms) may be present in the impure feed in an amount, or combined amount, of less than about 1 wt-%, or less than about 0.5 wt-%. In such embodiments, the amount, or combined amount, in the impure feed, of one or more compounds having only a single carbonyl carbon atom, may be within the ranges given above (e.g., from about 1 wt-% to about 75 wt-%).

More specific embodiments are directed to methods for increasing the amount, or effective availability, of glycolaldehyde that is generally initially present in an impure feed, but that may alternatively be absent or substantially absent in the impure feed. The impure feed may further comprise, for example, glyoxal, pyruvaldehyde, and hydroxyacetone (acetol). Contacting the impure feed with a hydrogenation catalyst under hydrogenation conditions as described herein converts (selectively hydrogenates) at least a portion of the glyoxal to form a product having an increased amount of glycolaldehyde as a first selectively hydrogenated analog. For example, the increased amount of glycolaldehyde may represent a yield, obtained from the conversion (selective hydrogenation) of glyoxal, within any of the ranges given above (e.g., at least about 60% of a theoretical yield) with respect to selectively hydrogenated analogs. Advantageously, the selective hydrogenation may be performed without any appreciable net formation of more completely, or completely, hydrogenated analogs, in which additional, or all, carbonyl carbon atoms are converted to hydroxyl carbon atoms. For example, the amount, in the product, of such analogs (e.g., ethylene glycol and/or propylene glycol) may represent a yield as described above (e.g., less than about 5%, less than about 2%, or less than about 1%, of a theoretical yield). Importantly, therefore, representative selective hydrogenation processes can be performed with little or no conversion of high value intermediates such as hydroxyacetone (acetol) to their completely hydrogenated analogs such as propylene glycol. In fact, the contacting under hydrogenation conditions may selectively hydrogenate at least a portion of the pyruvaldehyde, as a second starting compound, to form an increased amount of hydroxyacetone (acetol), as a major second selectively hydrogenated analog, in the product, together with the increased amount of glycolaldehyde.

Hydrogenation Catalysts and Conditions

Particular embodiments are directed to methods for selective hydrogenation as described above, according to which the impure feed is contacted with a hydrogenation catalyst under hydrogenation conditions. A representative hydrogenation catalyst is a noble metal-containing catalyst, meaning that it comprises at least one noble metal. For example, the hydrogenation catalyst may comprise ruthenium or platinum as a noble metal, or may comprise both of these noble metals. The hydrogenation catalyst may comprise either or both of these noble metals, or other noble metals, in an amount, or in a combined amount, generally from about 0.1 wt-% to about 15 wt-%, and typically from about 0.5 wt-% to about 10 wt-%, based on the weight of the catalyst. Regardless of the amount, the hydrogenation catalyst may be a solid supported noble metal-containing catalyst, meaning that the noble metal(s) is/are disposed on a solid support, which may be substantially refractory (inert) under the hydrogenation conditions, or which may itself be functional (e.g., in the case of providing acidic or basic sites to provide or promote catalytic activity). Carbon, including activated carbon, is an exemplary solid support.

Noble metals are understood as referring to a class of metallic elements that are resistant to oxidation. In representative embodiments, the at least one noble metal of the hydrogenation catalyst may be selected from the group consisting of platinum (Pt), rhodium (Rh), ruthenium (Ru), palladium (Pd), silver (Ag), osmium (Os), iridium (Ir), and gold (Au), with the term "consisting of" being used merely to denote group members, according to a specific embodiment, from which the noble metal(s) are selected, but not to preclude the addition of other noble metals and/or other metals generally. Accordingly, a hydrogenation catalyst comprising a noble metal embraces a catalyst comprising at least two noble metals, as well as a catalyst comprising at least three noble metals, and likewise a catalyst comprising two noble metals and a third, non-noble metal such as a promoter metal (e.g., a transition metal). According to preferred embodiments, the noble metal(s) is/are present in an amounts, or combined amounts, within the ranges given above. Alternatively, in the case of at least two noble metals being present, they may each independently be present in amounts from about 0.05 wt-% to about 12 wt-%, from about 0.3 wt-% to about 10 wt-%, or from about 1 wt-% to about 7.5 wt-%, based on the weight of the catalyst. Otherwise, a first noble metal may be present in an amount within any of these ranges, and a second noble metal may be present in a lower amount, compared to the first noble metal. For example, the second noble metal may be present in an amount from about 0.03 wt-% to about 10 wt-%, from about 0.1 wt-% to about 5 wt-%, or from about 0.3 wt-% to about 3 wt-%, based on the weight of the catalyst.

For example, a representative hydrogenation catalyst may comprise the two noble metals Ru and Pt, and the Ru and Pt may independently be present in an amount within any of these ranges (e.g., from about 1 wt-% to about 7.5 wt-%). That is, either the Ru may be present in such an amount, the Pt may be present in such an amount, or both Ru and Pt may be present in such amounts. In other embodiments, the Ru may be present in an amount within any of the ranges described above with respect to a first noble metal (e.g., from about 1 wt-% to about 7.5 wt-%), and the Pt may be present in an amount within any of the ranges described above with respect to a second noble metal (e.g., from about 0.3 wt-% to about 3 wt-%), with the Pt being present in a lower amount compared to the Ru.

In addition to one or more noble metals (e.g., Ru and Pt, in amounts described above), representative hydrogenation catalysts may further comprise a non-noble metal, such as metal selected from Groups 13-15 of the Periodic Table (e.g., Ga, Ge, In, or Sn). Such non-noble metal may be present in an amount within the ranges given above with respect to the noble metals (e.g., from about 0.05 wt-% to about 12 wt-%, from about 0.3 wt-% to about 10 wt-%, or from about 1 wt-% to about 7.5 wt-%, based on the weight of the catalyst). A preferred non-noble metal is Sn.

In representative embodiments, a single noble metal (e.g., either Ru or Pt), or otherwise two noble metals (e.g., both Ru and Pt), in either case being present with a non-noble metal selected from Groups 13-15 of the Periodic Table (e.g., Sn), may be substantially the only metals present in the hydrogenation catalyst, such that, for example, any other metal(s) is/are present in an amount or a combined amount of less than about 0.1 wt-%, or less than about 0.05 wt-%, based on the weight of the hydrogenation catalyst. In further representative embodiments, a single noble metal or two noble metals, together with the non-noble metal selected from Groups 13-15 of the Periodic Table (e.g., Sn), are substantially the only metals present in the hydrogenation catalyst, with the exception of metals that may be present in the solid support (e.g., such as aluminum being present in the solid support as aluminum oxide). Therefore, in the case of support comprising substantially all carbon, the single noble metal or two noble metals, together with the non-noble metal selected from Groups 13-15 of the Periodic Table (e.g., Sn), may be substantially the only metals present. For example, any other metal(s), besides the single noble metal or two noble metals, together with the non-noble metal selected from Groups 13-15 of the Periodic Table (e.g., Sn), and metals of the solid support (if any), may be present in an amount or a combined amount of less than about 0.1 wt-%, or less than about 0.05 wt-%, based on the weight of the hydrogenation catalyst. Any metals present in the catalyst, including noble metal(s), may have a metal particle size in the range generally from about 0.3 nanometers (nm) to about 20 nm, typically from about 0.5 nm to about 10 nm, and often from about 1 nm to about 5 nm.

The hydrogenation-active, noble metal(s), as well as non-noble metals (e.g., Sn), of representative hydrogenation catalysts may be disposed or deposited on a solid support, which is intended to encompass catalysts in which the metal(s) is/are on the support surface and/or within a porous internal structure of the support. Therefore, in addition to such hydrogenation-active metal(s), representative hydrogenation catalysts may further comprise a solid support, with exemplary solid supports comprising carbon and/or one or more metal oxides. Exemplary metal oxides are selected from the group consisting of aluminum oxide, silicon oxide, titanium oxide, zirconium oxide, magnesium oxide, strontium oxide, tin oxide, etc. The solid support may comprise all, or substantially all of the one or more of such metal oxides, for example such that the one or more metal oxides are present in an amount, or combined amount, of at least about 95 wt-% of the solid support. Alternatively, carbon, such as activated carbon, may be present in an amount of at least about 95 wt-%, or at least about 99 wt-%, of the solid support. Activated carbon refers to forms of carbon following any of a number of possible treatments (e.g., high temperature steaming) to increase porosity. Activated carbon also refers to forms obtained by chemical treatment (e.g., an acid or a base) to alter properties such as the concentration of acid sites.

The noble metal(s), as well as non-noble metals (e.g., Sn), may be incorporated in the solid support according to known techniques for catalyst preparation, including sublimation, impregnation, or dry mixing. In the case of impregnation, an impregnation solution of a soluble compound of one or more of the metals in a polar (aqueous) or non-polar (e.g., organic) solvent may be contacted with the solid support, preferably under an inert atmosphere. For example, this contacting may be carried out, preferably with stirring, in a surrounding atmosphere of nitrogen, argon, and/or helium, or otherwise in a non-inert atmosphere, such as air. The solvent may then be evaporated from the solid support, for example using heating, flowing gas, and/or vacuum conditions, leaving the dried, metal-impregnated support. The metal(s) may be impregnated in the solid support, such as in the case of two noble metals (e.g., Ru and Pt) and one non-noble metal (e.g., Sn) being impregnated simultaneously with both being dissolved in the same impregnation solution, or otherwise being impregnated separately using different impregnation solutions and contacting steps. In any event, the metal-impregnated support may be subjected to further preparation steps, such as washing with the solvent to remove excess noble metal(s) and impurities, further drying, calcination, etc. to provide the hydrogenation catalyst.

The solid support itself may be prepared according to known methods, such as extrusion to form cylindrical particles (extrudates) or oil dropping or spray drying to form spherical particles. Regardless of the specific shape of the solid support and resulting catalyst particles, the amounts of noble metal(s) and non-noble metal(s) being present in the hydrogenation catalyst, as described above, refer to the weight of such metal(s), on average, in a given catalyst particle (e.g., of any shape such as cylindrical or spherical), independent of the particular distribution of the metals within the particle. In this regard, it can be appreciated that different preparation methods can provide different distributions, such as deposition of the metal(s) primarily on or near the surface of the solid support or uniform distribution of the metal(s) throughout the solid support. In general, weight percentages described herein, being based on the weight of the solid support or otherwise based on the weight of hydrogenation catalyst, can refer to weight percentages in a single catalyst particle but more typically refer to average weight percentages over a large number of catalyst particles, such as the number in a hydrogenation reactor that form a catalyst bed as used in processes described herein.

Aspects of the present invention relate to methods for the selective hydrogenation of a starting compound such as glyoxal or pyruvaldehyde, using a noble metal-containing hydrogenation catalyst and hydrogenation conditions as described herein. Advantages associated with these methods are described above and include the formation of an additional amount of a desired selectively hydrogenated analog, without appreciable further conversion (hydrogenation) of such analog to a more completely, or completely hydrogenated analog. For any given impure feed, the amount and particular type of noble metal-containing hydrogenation catalyst and severity of the hydrogenation conditions, to achieve an optimal balance between selective hydrogenation of a starting compound without complete hydrogenation of the selectively hydrogenated analog produced, can be determined by those skilled in the art, with the knowledge gained from the present disclosure. Under hydrogenation conditions, the impure feed, including any solvent(s) such as water and/or methanol, may reside in combination with any hydrogenation catalyst described above, or combination of catalysts, to form a reaction mixture. The amount, or combined amount, of hydrogenation catalyst(s) in such reaction mixture may be from about 0.1 wt-% to about 10 wt-%, such as from about 0.3 wt-% to about 8 wt-% or from about 0.5 wt-% to about 5 wt-%. In the case of a continuous process, the hydrogenation catalyst(s) may be present in the reaction mixture in an amount needed to achieve a weight hourly space velocity (WHSV) as described below.

Typical hydrogenation conditions include an elevated total pressure and hydrogen partial pressure, with the latter often being at least about 3 megapascals (MPa) (435 psi). This hydrogen partial pressure, in combination with the noble metal-containing hydrogenation catalyst, can provide the performance criteria described above (e.g., in terms of relatively high yield(s) of one or more selectively hydrogenated analogs and relatively low yields of one or more completely hydrogenated analogs). The pressure may be contained in a hydrogenation reactor that is used for the contacting of the impure feed (e.g., an impure feed comprising glyoxal and/or pyruvaldehyde) with the heterogeneous (solid) noble metal-containing hydrogenation catalyst as described above, to obtain the product having an increased amount of selectively hydrogenated analog (e.g., glycolaldehyde or hydroxyacetone (acetol)). The reaction mixture, which includes the catalyst and which is subjected to the hydrogenation conditions, may be aqueous (comprise water as a solvent) or organic (e.g., comprise methanol as a solvent) and generally comprises dissolved hydrogen under these conditions. In the case of a continuous process, the impure feed may be added continuously to the reaction mixture and the product may be withdrawn continuously from the reaction mixture (e.g., following separation from the catalyst(s)).

Hydrogenation conditions, under which the reaction mixture is maintained during the conversion of starting compound(s) to respective, selectively hydrogenated analog(s), include an absolute reactor pressure in the range generally from about 2.07 MPa (300 psi) to about 24.1 MPa (3500 psi), typically from about 3.45 MPa (500 psi) to about 20.7 MPa (3000 psi), and often from about 5.17 MPa (750 psi) to about 10.3 MPa (1500 psi). The reactor pressure may be generated predominantly or substantially from hydrogen, such that these ranges of total pressure may also correspond to ranges of hydrogen partial pressure. However, the contribution of the vapor pressure of the reaction mixture to the total pressure under the hydrogenation conditions will generally result in the hydrogen partial pressure being reduced relative to the total pressure, such that, for example, the hydrogen partial pressure may range generally from about 1.38 MPa (200 psi) to about 22.4 MPa (3250 psi), typically from about 3.00 MPa (435 psi) to about 20.0 MPa (2901 psi), and often from about 4.82 MPa (700 psi) to about 9.31 MPa (1350 psi).

Other hydrogenation conditions, present in the hydrogenation reactor, include a temperature generally from about 20° C. (68° F.) to about 200° C. (392° F.), typically from about 50° C. (122° F.) to about 150° C. (302° F.), and often from about 50° C. (122° F.) to about 75° C. (167° F.). The reaction time, i.e., time at which the reaction mixture is maintained under conditions of pressure and temperature at any target values or target sub-ranges within any of the ranges of pressure and temperature given above (e.g., a target, total pressure value of 8.27 MPa (1200 psi) and a target temperature of 65° C. (149° F.)), is generally from about 0.25 hours to about 15 hours, typically from about 0.25 hours to about 5 hours, and often from about 0.5 hours to about 3 hours, in the case of a batchwise reaction. For a continuous process, these reaction times correspond to reactor residence times. An additional parameter that is relevant for a continuous process is weight hourly space velocity (WHSV), which is understood in the art as the weight flow of the feed (e.g., the impure feed comprising the starting compound(s)) to a reactor, divided by the weight of the catalyst, in this case the noble metal-containing hydrogenation catalyst. This parameter therefore represents the equivalent catalyst bed weight of the feed processed every hour, and it is related to the inverse of the reactor residence time. According to representative embodiments, the hydrogenation conditions include a WHSV generally from about 0.01 $hr^{-1}$ to about 20 $hr^{-1}$, typically from about 0.05 $hr^{-1}$ to about 5 $hr^{-1}$, and often from about 0.5 $hr^{-1}$ to about 3 $hr^{-1}$.

Using the teachings herein, the skilled person can adjust hydrogenation conditions to an optimal severity for a given impure feed and hydrogenation catalyst, such that starting compound(s) are selectively hydrogenated to corresponding, selectively hydrogenated analogs as described herein, but not substantially converted to their corresponding, more completely or completely hydrogenated analogs. For example, hydrogenation severity can be increased by increasing any one or more of hydrogen partial pressure, temperature, and residence time (or by decreasing WHSV in the case of a continuous process). Conversely, hydrogenation severity can be decreased by decreasing any one or more of these hydrogenation conditions (or by increasing WHSV in the case of a continuous process). Representative embodiments are therefore directed to selective hydrogenation processes as described herein, further comprising monitoring the composition of the product (e.g., to determine the concentration of a given starting compound, selectively hydrogenated analog, and/or completely hydrogenated analog), and, based on such composition, adjusting hydrogenation severity to improve or optimize this composition (e.g., decrease or minimize a concentration of a starting compound or completely hydrogenated analog, or increase or maximize a concentration of a selectively hydrogenated analog).

The impure feed may be charged to the hydrogenation reactor batchwise, or may otherwise be continuously added to this reactor. In either case, the use of a heterogeneous (solid) hydrogenation catalyst facilitates the separation of the product, generally obtained as a liquid (following cooling), from the reaction mixture comprising this catalyst. In the case of batchwise operation, following charging of the impure feed and hydrogenation catalyst to the selective hydrogenation reactor, the reactor may be sealed, purged with inert gas (e.g., nitrogen), and then purged and pressurized with hydrogen. In the case of continuous operation, the impure feed may be continuously added (e.g., pumped) to the reactor, following such purging a pressurization. A fresh hydrogen stream may also be continuously added, and this fresh hydrogen stream may optionally be combined with a recycle gas stream comprising hydrogen, such that a combined (fresh and recycle) hydrogen stream may be continuously added (e.g., using one or more compressors, such as a feed compressor and a recycle compressor) to the reactor. The recycle gas stream may be all or a portion (e.g., following the removal of a vent or purge gas stream to prevent excessive accumulation of unwanted impurities) of a vapor fraction that is separated from the product and, like the product, is continuously withdrawn from the reactor. For example, the vapor fraction comprising the recycle gas stream and a liquid fraction comprising the product, may be withdrawn together from the reactor in a reactor effluent stream that is substantially free of the catalyst. To improve recovery of condensable species (e.g., selectively hydrogenated analogs and/or unconverted starting compounds) in the liquid fraction/product, the reactor effluent stream may be cooled (e.g., using a condenser), prior to separation of the vapor fraction from the liquid fraction (e.g., in a flash separator). According to some embodiments, a portion of the product may likewise be recycled to the reactor (e.g., following one or more downstream separation steps), in order to improve overall conversion of a given starting compound to a selectively hydrogenated analog. In the case of a batchwise reaction, hydrogen is generally present in the reactor in a stoichiometric excess of the molar hydrogen requirement for complete conversion of the one or more starting compounds to their selectively hydrogenated analogs. For example, the stoichiometric excess may represent at least 1.5 times, at least 5 times, or at least 10 times, this molar hydrogen requirement. In the case of a continuous reaction, hydrogen is generally added (e.g., in the fresh hydrogen stream or in a combined hydrogen stream) in such stoichiometric excess.

The product recovered from the hydrogenation reactor may be subjected to any of a number of possible separation steps to provide purified product streams, such as those enriched in any of the selectively hydrogenated analogs described herein (e.g., glycolaldehyde, hydroxyacetone (acetol), and/or 2-hydroxy propanal). Such separation steps may include one or more of phase separation, extraction (e.g., using an organic solvent having preferential affinity for a selectively hydrogenated analog), and distillation, sequentially in any order. Extraction and distillation may alternatively be combined in a single, extractive distillation step. As described above, certain advantages of selective hydrogenation methods described herein reside in the conversion of starting compounds to their selectively hydrogenation analogs, having significantly different relative volatility and thereby being more easily separable, such as in a high-boiling fraction obtained by distillation. For example, the starting compound glyoxal has a normal boiling point of 51° C. (124° F.), whereas its selectively hydrogenated analog glycolaldehyde has a significantly greater normal boiling point of 131° C. (268° F.). The starting compound pyruvaldehyde has a normal boiling point of 72° C. (162° F.), whereas its selectively hydrogenated analog hydroxyacetone (acetol) has a significantly greater normal boiling point of about 146° C. (295° F.) and its selectively hydrogenated analog 2-hydroxy propanal also has a significantly greater normal boiling point of about 122° C. (252° F.). As with the recycle gas stream, any separated liquid product stream(s), particularly such streams being enriched in one or more unconverted starting compounds, may likewise be recycled to the hydrogenation reactor.

According to further embodiments, the production of one or more selectively hydrogenated analogs such as glycolaldehyde and/or hydroxyacetone (acetol) may be integrated with upstream and/or downstream processing steps, such as in processes for pyrolysis of carbohydrates (e.g., aldose-containing sugars). Upstream processing may therefore include pyrolyzing an aqueous solution of a carbohydrate in a pyrolysis reactor under pyrolysis conditions, including elevated temperature (e.g., 500° C. (932° F.) or greater), to provide a vapor phase pyrolysis product comprising thermal decomposition products of the aldose-containing sugar. This may further include cooling the vapor phase pyrolysis product, for example in a condenser, to condense a liquid mixture comprising, as such thermal decomposition products, glyoxal, pyruvaldehyde, glycolaldehyde, and hydroxyacetone (acetol). The condensed liquid mixture, obtained from such upstream processing steps, may then correspond to an impure feed as described herein.

Production methods may therefore further comprise contacting the condensed liquid mixture with a hydrogenation catalyst under hydrogenation conditions, to selectively hydrogenate (i) at least a portion of the glyoxal, (ii) at least a portion of the pyruvaldehyde, or (iii) both (i) and (ii) to form a product having respectively, (i) an increased amount of glycolaldehyde, (ii) an increased amount of hydroxyacetone (acetol), or (iii) both (i) and (ii). These selectively hydrogenated analogs, namely glycolaldehyde and hydroxyacetone (acetol), by virtue of their increased boiling points relative to their respective starting compounds, glyoxal and pyruvaldehyde, may be conveniently separated by distillation of the product. In particular, downstream processing may comprise distilling the product to recover a fraction, such as a bottoms fraction or a relatively high-boiling fraction that is enriched in, respectively, (i) glycolaldehyde (a glycolaldehyde-enriched fraction), (ii) hydroxyacetone (acetol) (a hydroxyacetone-enriched fraction), or (iii) both (i) and (ii) (a glycolaldehyde and hydroxyacetone-enriched fraction). In this case, the term "enriched in" refers to an increased concentration or percentage by weight of (i), (ii), or (iii), at least relative to the product, which may in this case correspond to the feed to the distillation. The distilling of the product may further recover a fraction, such as an overhead fraction or a relatively low-boiling fraction that is depleted in, respectively, (i) glycolaldehyde (a glycolaldehyde-depleted fraction), (ii) hydroxyacetone (acetol) (a hydroxyacetone-depleted fraction), or (iii) both (i) and (ii) (a glycolaldehyde and hydroxyacetone-depleted fraction). In this case, the term "depleted in" refers to a decreased concentration or percentage by weight of (i), (ii), or (iii), at least relative to the product, which may in this case correspond to the feed to the distillation. In some embodiments, such overhead fraction or relatively low-boiling fraction may be enriched, relative to the product, in one or more respective starting compounds, such as enriched in (iv) unconverted glyoxal, (v) unconverted pyruvaldehyde, or (vi) both (iv) and (v). Depending on the particular concentration or percentage by weight of (iv), (v), or (vi), overall conversion and process economics may be improved by recycling, to the hydrogenation reactor, at least a portion of such overhead fraction or relatively low-boiling fraction, or otherwise at least a portion of any other fraction obtained in the production method and having sufficient concentration or percentage by weight of (iv), (v), or (vi), to justify its recycle to the hydrogenation reactor The following examples are set forth as representative of the present invention. These examples are not to be construed as limiting the scope of the invention as other equivalent embodiments will be apparent in view of the present disclosure and appended claims.

Example 1

Hydrogenation of Furfural

A liquid mixture of 24 grams of furfural and 62 grams of methanol solvent was charged to a 300 cc high pressure reactor (Parr Instrument Company). To this mixture was added 2.05 grams of particulate, solid catalyst with the metal contents of 2 wt-% Ru/2 wt-% Sn/0.5% wt-% Pt, disposed on a carbon support. The reactor was purged with hydrogen (3×500 psi) while continuously stirring the reaction mixture at 800 rpm. Thereafter, the reactor was pressurized with hydrogen to 1200 psi, and the reaction mixture was heated to 65° C. and maintained at this temperature for 1 hour. The reaction mixture was then cooled to room temperature and the reactor was opened. The solid and liquid contents were removed from the reactor and filtered by vacuum filtration to separate the catalyst. The filtrate was subjected to rotary evaporation to remove the methanol solvent. The remaining liquid was analyzed for its composition using nuclear magnetic resonance (NMR) spectroscopy and was found to contain furfural alcohol (5-hydroxymethylfuran) and unreacted furfural.

The hydrogenation catalyst and conditions were therefore sufficient to hydrogenate a portion of the furfural to its corresponding hydrogenated analog, 5-hydroxymethylfuran.

Example 2

Selective Hydrogenation of Pyruvaldehyde

A liquid composition of 15.1 grams of pyruvaldehyde, concentrated to 40 wt-% in water, was added to 86 ml of water, and the resulting mixture was charged to a 300 cc high pressure reactor (Parr Instrument Company). To this mixture was added 1.96 grams of particulate, solid catalyst with the metal contents of 2 wt-% Ru/2 wt-% Sn/0.5% wt-% Pt, disposed on a carbon support. The reactor was purged with hydrogen (3×500 psi) while continuously stirring the reaction mixture at 800 rpm. Thereafter, the reactor was pressurized with hydrogen to 1200 psi, and the reaction mixture was heated to 65° C. and maintained at this temperature for 1 hour. The reaction mixture was then cooled to room temperature and the reactor was opened. The solid and liquid contents were removed from the reactor and filtered by vacuum filtration to separate the catalyst. The filtrate was analyzed for its composition using NMR spectroscopy and was found to contain mostly (>80%) hydroxyacetone (acetol) and a small amount of unconverted pyruvaldehyde.

The hydrogenation catalyst and conditions were therefore sufficient to selectively hydrogenate the pyruvaldehyde to its selectively hydrogenated analog, hydroxyacetone (acetol).

Example 3

Selective Hydrogenation of Glyoxal

A liquid composition of 15.1 grams of glyoxal, concentrated to 40 wt-% in water, was added to 85 ml of water, and the resulting mixture was charged to a 300 cc high pressure reactor (Parr Instrument Company). To this mixture was added 2.17 grams of particulate, solid catalyst with the metal contents of 2 wt-% Ru/2 wt-% Sn/0.5% wt-% Pt, disposed on a carbon support. The reactor was purged with hydrogen (3×500 psi) while continuously stirring the reaction mixture at 800 rpm. Thereafter, the reactor was pressurized with hydrogen to 1200 psi, and the reaction mixture was heated to 60° C. and maintained at this temperature for 1 hour. The reaction mixture was then cooled to room temperature and the reactor was opened. The solid and liquid contents were removed from the reactor and filtered by vacuum filtration to separate the catalyst. The filtrate was analyzed for its composition using NMR spectroscopy and was found to contain glycolaldehyde (14%, based on NMR) and unconverted glyoxal.

The hydrogenation catalyst and conditions were therefore sufficient to selectively hydrogenate the glyoxal to its selectively hydrogenated analog, glycolaldehyde.

Example 4

Selective Hydrogenation of Glyoxal and Pyruvaldehyde

A liquid composition of 100 ml, containing 7 wt-% glycolaldehyde, and also containing glyoxal and pyruvaldehyde, was charged to a 300 cc high pressure reactor (Parr Instrument Company). To this mixture was added 2.05 grams of particulate, solid catalyst with the metal contents of 2 wt-% Ru/2 wt-% Sn/0.5% wt-% Pt, disposed on a carbon support. The reactor was purged with hydrogen (3×500 psi) while continuously stirring the reaction mixture at 800 rpm. Thereafter, the reactor was pressurized with hydrogen to 1200 psi, and the reaction mixture was heated to 60° C. and maintained at this temperature for 1 hour. The reaction mixture was then cooled to room temperature and the reactor was opened. The solid and liquid contents were removed from the reactor and filtered by vacuum filtration to separate the catalyst. The filtrate was analyzed for its composition using NMR spectroscopy and was found to contain glycolaldehyde and hydroxyacetone (acetol). Ethylene glycol was also detected, but only at a trace level of less than 100 parts per million (ppm) by weight.

The hydrogenation catalyst and conditions were therefore sufficient to selectively hydrogenate the glyoxal to its selectively hydrogenated analog, glycolaldehyde, and also selectively hydrogenate the pyruvaldehyde to its selectively hydrogenated analog, hydroxyacetone (acetol). Under the same conditions, almost none of the completely hydrogenated analog of glyoxal, namely ethylene glycol, was produced.

Overall, aspects of the invention relate to the use of selective hydrogenation to increase the concentration of certain desired intermediates, such as glycolaldehyde and hydroxyacetone (acetol), in impure feeds, such as liquid mixtures recovered from carbohydrate pyrolysis. Efficiencies and the associated economics of synthesis pathways from renewable feeds, through such desired intermediates, and to high value chemicals are thereby improved. Those having skill in the art, with the knowledge gained from the present disclosure, will recognize that various changes can be made to the disclosed catalysts and processes in attaining these and other advantages, without departing from the scope of the present disclosure. As such, it should be understood that the features of the disclosure are susceptible to modifications and/or substitutions. The specific embodiments illustrated and described herein are for illustrative purposes only, and not limiting of the invention as set forth in the appended claims.

What is claimed is:

1. A method for increasing the amount of glycolaldehyde present in an impure feed comprising glyoxal, pyruvaldehyde, glycolaldehyde, and hydroxyacetone (acetol), the method comprising contacting the impure feed with a hydrogenation catalyst under hydrogenation conditions, to selectively hydrogenate at least a portion of the glyoxal to form a product having an increased amount of glycolaldehyde.

2. The method of claim 1, wherein the contacting under hydrogenation conditions selectively hydrogenates at least a portion of the pyruvaldehyde to form an increased amount of hydroxyacetone in the product, together with the increased amount of glycolaldehyde.

3. A method for producing glycolaldehyde and/or hydroxyacetone (acetol), the method comprising:

pyrolyzing an aqueous solution of an aldose-containing sugar in a pyrolysis reactor under pyrolysis conditions, including elevated temperature, to provide a vapor phase pyrolysis product comprising thermal decomposition products of the aldose-containing sugar;

cooling said vapor phase pyrolysis product to condense a liquid mixture comprising glyoxal, pyruvaldehyde, glycolaldehyde, and hydroxyacetone (acetol);

contacting the liquid mixture with a hydrogenation catalyst under hydrogenation conditions, to selectively hydrogenate (i) at least a portion of the glyoxal, (ii) at least a portion of the pyruvaldehyde, or (iii) both (i) and (ii) to form a product having respectively, (i) an increased amount of glycolaldehyde, (ii) an increased amount of hydroxyacetone (acetol), or (iii) both (i) and (ii); and distilling the product to recover a fraction that is enriched in, respectively, (i) glycolaldehyde, (ii) hydroxyacetone (acetol), or (iii) both (i) and (ii).

* * * * *